(12) United States Patent
Charng

(10) Patent No.: US 8,524,979 B2
(45) Date of Patent: Sep. 3, 2013

(54) TERMINATION OF TRANSGENE EXPRESSION VIA TRANSPOSON-MEDIATED BREAK

(75) Inventor: Yuh-Chyang Charng, Taipei (TW)

(73) Assignee: National Taiwan University, Taipei (TW)

( * ) Notice: Subject to any disclaimer, the term of this patent is extended or adjusted under 35 U.S.C. 154(b) by 1116 days.

(21) Appl. No.: 12/102,266

(22) Filed: Apr. 14, 2008

(65) Prior Publication Data

US 2009/0260103 A1  Oct. 15, 2009

(51) Int. Cl.
  *C12N 15/82*  (2006.01)
  *C12N 15/87*  (2006.01)
  *C12N 15/29*  (2006.01)
  *C12N 15/52*  (2006.01)
  *A01H 1/04*  (2006.01)

(52) U.S. Cl.
  CPC ........ *C12N 15/8237* (2013.01); *C12N 15/8265* (2013.01); *C12N 15/8238* (2013.01); *C12N 15/8209* (2013.01)
  USPC ..... 800/291; 800/300; 800/320.1; 800/320.2; 800/323; 800/287; 536/23.2; 536/23.6; 536/24.1

(58) Field of Classification Search
  None
  See application file for complete search history.

(56) References Cited

U.S. PATENT DOCUMENTS 7,144,734 B2 * 12/2006 Court et al. .................. 435/471
7,196,244 B1 *  3/2007 Bessereau et al. ............. 800/21

FOREIGN PATENT DOCUMENTS

WO         01/96583         12/2001

OTHER PUBLICATIONS

Ebinuma et al. Proceedings of the National Academy of Science USA 94(6): 2117-2121 (Mar. 1997).*
Charng et al. Molecular Breeding 6(4): 353-367 (Aug. 2000).*
Brian Miki et al.; Selectable marker genes in transgenic plants: applications, alternatives and biosafety; Journal; 2004; pp. 193-232; vol. 107; Journal of Biotechnology; Science Direct; Elsevier B.V.
Y. Sha et al.; Generation and flanking sequence analysis of a rice T-BNA tagged population; Journal; 2003; pp. 306-314; vol. 108; Theor. Appl. Genet.; Springer-Verlag.
Yuh-Chyang Charng et al.; The inducible transposon system for rice functional genomics; Journal; 2007; pp. 1-11; vol. 48; Botanical Studies; Molecular Biology.
Behrooz Darbani et al.; Methods to produce marker-free transgenic plants; Journal; 2007; pp. 83-90; vol. 1; Biotechnology Journal; Wiley-VCH Verlag GmbH& Co. KGaA, Weinheim.
Arlene R. Howe et al.; Glyphosate as a selective agent for the production of fertile transgenic maize (*Zea mays* L.) plants; Journal; 2002; pp. 153-164; vol. 10; Molecular Breeding; Kluwer Academic Publishers; Netherlands.
Peter T. J. Hajdukiewicz et al; Multiple pathways for Cre/lox-mediated recombination in plastids; Journal; 2001; pp. 161-170; vol. 27, No. 2; Technical Advance; The Plant Journal; Blackwell Science Ltd.
Yuh-Chyang Charng, Investigation of inducible transposon to remove selection marker, Master Thesis Graduate Institute of Agronomy National Taiwan University, Jul. 2005, pp. 1-70.

* cited by examiner

*Primary Examiner* — David T Fox
(74) *Attorney, Agent, or Firm* — WPAT, P.C.; Anthony King

(57) ABSTRACT

This invention provides a genetic construct comprising: (a) a DNA cut-and-paste transposon genetic unit which comprises a transposase gene flanked on either side by inverted repeat sequences and operably under the control of a first promoter; and (b) a transgene unit which comprises an expressable transgene, placed operably under the control of a second promoter; wherein the transposon genetic unit and the transgene unit are linked with one of the inverted repeat sequence located in an intron of the transgene. This invention also provides methods of transiently expressing a transgene in a stably transformed eukaryote. This invention further provides methods for obtaining marker-free transgenic plants.

14 Claims, 12 Drawing Sheets

TERMINATION OF TRANSGENE EXPRESSION VIA TRANSPOSON-MEDIATED BREAK

FIELD OF THE INVENTION

This invention relates to a genetic construct comprising: (a) a DNA cut-and-paste transposon genetic unit which comprises a transposase gene flanked on either side by inverted repeat sequences and operably under the control of a first promoter; and (b) a transgene unit which comprises an expressable transgene, placed operably under the control of a second promoter; wherein the transposon genetic unit and the transgene unit are linked with one of the inverted repeat sequence located in an intron of the transgene.

This invention also relates methods of transiently expressing a transgene in a stably transformed eukaryote.

This invention further relates to methods for obtaining marker-free transgenic plants.

BACKGROUND OF THE INVENTION

Transposition, the movement of genes from one position to another within the genome, was first suggested by Barbara McClintock. These moveable genes are also knows as jumping genes, transposable elements, or transposons. They exist in all organisms (eukaryotes, prokaryotes, and viruses). Transposons are classified into two classes based on their mechanism of transposition. Retrotransposons (class 1) work by copying themselves and pasting copies back into the genome in multiple places. Initially retrotransposons copy themselves to RNA (transcription) but, in addition to being transcribed, the RNA is copied into DNA by a reverse transcriptase (often coded by the transposon itself) and inserted back into the genome. DNA transposons (class 2) do not involve an RNA intermediate. DNA fragments transpose directly from DNA segment to DNA segment: producing a DNA copy that transposes (replicative transposition or copy-and-paste mechanism) or cut/paste the transposon itself into a new locus (conservative transposition or cut- and paste mechanism) via a transposase encoded by the transposon. Maize Ac transposon, En/Spm transposon, Mutator (Mu) transposon, *Drosophila* P element, piggyBac transposon, and mice Sleeping Beauty (SB) transposon employ a cut-and-paste mechanism.

The maize transposon Activator (Ac) is an autonomous transposable element of 4,565 bp active in a wide range of plant species. It codes for a single gene product, Ac transposase. The transposase gene is flanked on either side by inverted repeat sequences (IR), which are essential for transposition.

The genetic modification of plants offers improvements in agricultural practices, food safety, and human health. The development of transgenic plants requires the use of selectable marker genes, because the efficiency of plant transformation is less than optimal for many important plant species. In current plant transformation systems, a selectable marker gene is co-delivered with the gene of interest (GOI) to identify and separate rare transgenic cells from non-transgenic cells. Usually, a conditional dominant gene, with no influence on the growth or morphology of plants, is used as a selectable marker. Dominant genes encoding either antibiotic or herbicide resistance are widely used as selectable markers.

The antibiotics and herbicides used to select rare transgenic cells from non-transgenic cells generally have negative effects on proliferation and differentiation. For example, glyphosate inhibits 5-enolpyruvylshikimate-3-phosphate synthase (EPSPS), a critical enzyme in the shikimate pathway for the biosynthesis of aromatic amino acids. Glyphosate-resistant epsps was successfully used as a selectable marker in the plant transformation of oilseed rape, soybean, potato, maize, and wheat.

Over the past few years, consumer and environmental groups have expressed concern about the use of markers from an ecological and food safety perspective. The development of marker-free transgenic plants is desirable in agricultural biotechnology. Many strategies to produce markerfree transgenic plants have been described. The Cre-lox site-specific recombination system has been widely studied for marker removal. In fact, the first markerfree commercial transgenic plant was developed using Cre-lox technology. In the transformation vector, the marker is flanked by directly oriented lox sites. A cre gene is introduced into the genome from a genetic cross. The expression of the Cre protein causes recombination between the two loxP sites, and the marker is lost during the process of recombination. New techniques have been developed to control the cre gene expression by flanked with an inducible promoter. A limitation of this system is that the high level of expression of the cre gene may result in phenotypic aberrations in some plant species (Hajdukiewicz et al. 2001). In contrast to the Cre-lox recombination system leading to the loss of the marker gene, the transposon system (e.g., Ac/Ds) offers information about the new location of the removed marker's DNA. In the transformation vector, the marker gene is inserted into the Ds element. The expression of the Ac transposase excises both ends of the transposon and usually re-integrates into other locations on the chromosome. When the transposon transposes within the same chromosome (linked transposition), both insertion sites of the T-DNA (harboring the marker gene) and the transposon (harboring the GOI) need regulatory approval for commercialization. With unlinked transposition, the marker gene can be removed by out-crossing. Although the work is time consuming, all removed information remains clear for regulatory approval. Furthermore, with the transposon system, one successful transformation can create more independent transgenic lines because of the re-integrated loci. This feature is valuable for creating transgenic plants in species with low transformation efficiency. However, out-crossing with this system cannot be used with vegetatively propagated plants and woody tree species.

US2007259430, WO0196583, US2007220627 disclose processes for removing the selectable marker gene via homologous recombination system, wherein US2007259430 and US2007220627 refer to exchange between specific recombinase recognition sequence.

U.S. Pat. No. 5,482,852 discloses biologically safe plant transformation system via crossing the transformed plant through self-crossing or with another plant to obtain F1 or more removed generation progeny; and utilizing a means for selecting those progeny that carry the gene of interest and are free of the ancillary nucleic acids.

SUMMARY OF THE INVENTION

Figure 1:
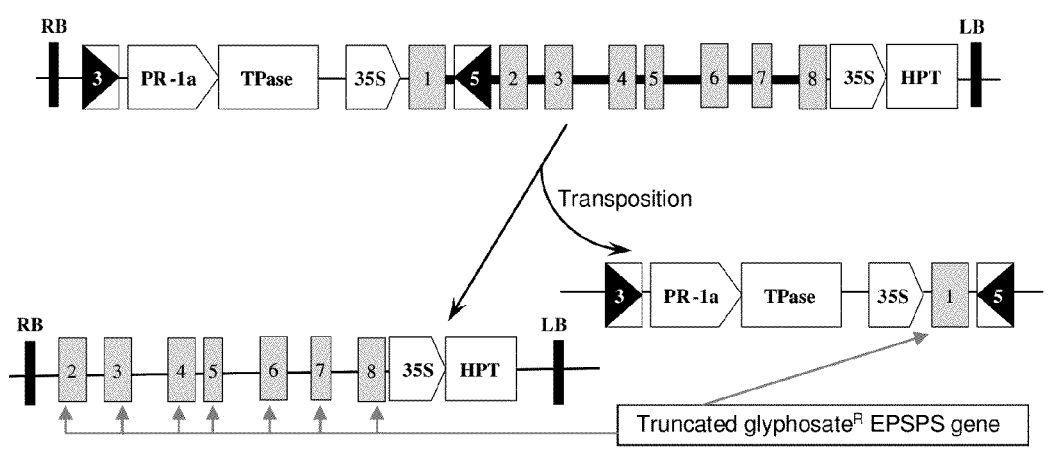
FIG. 1 shows strategy for termination of selectable marker (glyphosateR EPSPS) gene; LB, left border; RB, right border; 5' and 3', Ac left and right terminal-inverted repeat; PR-1a inducible promoter; TPase, transposase; 35S, The cauliflower mosaic virus 35S RNA promoter; 1-8, EPSPS exon 1-exon 8.

This invention provides a genetic construct comprising: (a) a DNA cut-and-paste transposon genetic unit which comprises a transposase gene flanked on either side by inverted repeat sequences and operably under the control of a first promoter; and (b) a transgene unit which comprises an expressable transgene, placed operably under the control of a second promoter; wherein the transposon genetic unit and the transgene unit are linked with one of the inverted repeat sequence located in an intron of the transgene.

This invention also provides methods of transiently expressing a transgene in a stably transformed eukaryote.

This invention further provides methods for obtaining marker-free transgenic plants.

DETAILED DESCRIPTION OF THE INVENTION

In the present invention, a system to truncate a transgene such as a marker gene after transposition has been designed. This system does not require segregating the transgene away, and thus is well applicable to vegetatively propagate plants and woody tree species. The system involves introducing an intron-containing transgene, accompanied by a transposon whose one end is located in the intron of the transgene, into a transformation vector. The prerequisite of the strategy is to obtain an intron-containing transgene. The intron can be inherent or artificial.

On the other hand, the transposon usually undergoes further transposition, even under the control of an inducible promoter, this phenomenon sometimes happens, possibly because of endogenous stimuli. Thus, the system is further modified to resolve this more-than-one-time transposition by locating the other end of the transposon in the transposase gene's intron.

Accordingly, the present invention provides a genetic construct comprising:
  (a) a DNA cut-and-paste transposon genetic unit which comprises a transposase gene flanked on either side by inverted repeat sequences and operably under the control of a first promoter; and
  (b) a transgene unit which comprises an expressable transgene placed operably under the control of a second promoter;
  wherein the transposon genetic unit and the transgene unit are linked with one of the inverted repeat sequences located in an intron of the transgene.

In one embodiment, the first promoter is an inducible promoter which can be induced by chemicals, stress, light or any other environmental factors.

In another embodiment, the inverted repeat sequence other than the one located in the intron of the transgene further located in an intron of the transposase gene.

The transposon of the present invention can be any cut-and-paste transposon, such as, but not limited to, maize Ac transposon, En/Spm transposon, Mutator (Mu) transposon, *Drosophila* P element, piggyBac transposon, or mice Sleeping Beauty (SB) transposon.

In one preferred embodiment, the transposon is maize Ac transposon, the transposase gene is Ac transposase gene, the inverted repeat sequences are Ac left and right terminal-inverted repeat.

Previously, the Ac transposase gene was fused with the promoter of the pathogenesis-related protein 1a (PR-1a).

PR-1 proteins are induced in plants as a consequence of the hypersensitive defense reaction elicited by pathogen infection, by exogenous application of some chemicals, e.g., salicylic acid (SA), and by developmental stimuli. In one preferred embodiment, the first promoter is PR-1a inducible promoter.

In one embodiment, the second promoter is 35S RNA promoter.

In one embodiment, the transgene is a selectable marker.

The present invention also provides a method of transiently expressing a transgene in a stably transformed eukaryote, comprising:
(a) stably transforming the eukaryote with the genetic construct, comprising
  (i) a DNA cut-and-paste transposon genetic unit which comprises a transposase gene flanked on either side by inverted repeat sequences and operably under the control of a first promoter; and
  (ii) a transgene unit which comprises an expressable transgene, placed operably under the control of a second promoter;
  wherein the transposon genetic unit and the transgene unit are linked with one of the inverted repeat sequence located in an intron of the transgene;
(b) expressing the transgene of the genetic construct in the eukaryote; and
(c) expressing the transposase gene of the genetic construct in the eukaryote.

In one embodiment, the step (c) of the said method is inducible when the first promoter of the genetic construct in the step (a) is an inducible promoter and applying a corresponding inducing agent of the inducible promoter to the eukaryote at the step (c). In another embodiment, the expression of the transposase gene is able to be induced only one-time when the inverted repeat sequence other than the one located in the intron of the transgene further located in an intron of the transposase gene.

In one embodiment, the eukaryote is a plant.

In a preferred embodiment, the plant is maize, rice, fruit or flower.

The present invention also provides a method for obtaining marker-free transgenic plants, comprising:
(a) stably transforming the plant with the genetic construct, comprising:
  (i) a DNA cut-and-paste transposon genetic unit which comprises a maize Ac transposase gene flanked on either side by inverted repeat sequences and operably under the control of a first promoter;
  (ii) a transgene unit which comprises a selectable marker gene placed operably under the control of a second promoter, and a gene of interest linked to the selectable marker gene and placed operably under the control of a third promoter;
  wherein the transposon genetic unit and the transgene unit are linked with one of the inverted repeat sequence located in an intron of the selectable marker gene;
(b) delivering the construct of the step (a) to a plant;
(c) expressing the transgene unit of the genetic construct in the plant; and
(d) expressing the transposase gene of the genetic construct in the plant.

In one embodiment, the step (d) is inducible when the first promoter of the genetic construct is an inducible promoter and applying a corresponding inducing agent of the inducible promoter to the plant at the step (d). In another embodiment, the expression of the transposase gene is able to be induced only one-time when the inverted repeat sequence other than the one located in the intron of the selectable marker gene further located in an intron of the transposase gene.

In one preferred embodiment, the step (a) is accomplished by an *Agrobacterium* strain.

In one preferred embodiment, the plant is maize, rice, fruit or flower.

In one preferred embodiment, the transposase gene in the method is maize Ac transposase gene.

EXAMPLE

The examples below are non-limiting and are merely representative of various aspects and features of the present invention.
Materials and Methods
Modification of the Rice epsps
Plasmid p6140 containing a genomic copy of epsps from rice was obtained from Dr. Kishima (Hokkaido University, Japan). To construct a gene for the glyphosate-tolerant form of the EPSPS enzyme, site-directed mutagenesis was used to change two codons in the coding sequence as described previously (Howe et al., Glyphosate as a selective agent for the production of fertile transgenic maize plants. 2002, Mol Breed 10: 153-164), whereby the authors modified the corn epsps cDNA clone for a glyphosate-tolerant form. The DNA fragment containing exons 2-4 was firstly sub-cloned into plasmid pBC. The codon for the glycine residue at position 168 was changed to encode an alanine residue and that for the glycine residue at position 211 was changed to encode an aspartic acid residue by polymerase chain reaction (PCR) as described. The resulting DNA fragment, together with the other epsps exons, was used for subsequent construction.
DNA Manipulation and Plant Transformation
The construction procedures for the KCEH system (KCEH transposon plus the marker gene): All cloning and DNA manipulations followed standard procedures with the use of chemicals from Roche (Basel, Switzerland). All transformations involved the use of rice (*Oryza sativa* L. cv. TNG67) as described.

The construction procedures for the COYA system: All cloning and DNA manipulations followed standard procedures with use of chemicals from Roche (Basel, Switzerland). All transformations involved use of rice (*Oryza sativa* L. cv TNG67) as described.
Assay of T1 Progeny Resistant to Glyphosate
Successful transgenic plants resistant to glyphosate were self-pollinated to obtain T1 seeds. The seeds were imbibed in flowing water for 2 days, then transferred to an iron grid and kept in water for 2 weeks, and then soil for another week. The three leaf-age stage rice seedlings were sprayed once with 5,000 ppm Roundup®. The effect could be observed after 1 week.
RT-PCR Analysis of epsps Expression
RNA extracted from the transgenic rice calli was reverse-transcribed with use of the SuperScript™ First-Strand Synthesis System (Invitrogen). Primers specific to each of the two target messages were used in subsequent PCR amplification: R-E1FC (5'-ATCGTGCTCCAGCCCATCAG-3') (SEQ ID NO:1), mKRT1F (5'-CAACTCTTCTTGG GGAACGCT-GCT-3') (SEQ ID NO:2), and mKRT2R (5'-CAAGGAAA-CAGTCG ACATCCGCGT-3') (SEQ ID NO:3). Primers specific to endogenous epsps were KRT1F (5'-CAACTCTTCTTGGGGAACGCTGGA-3') (SEQ ID NO:4) and KRT2R (5'-CAAGGAA ACAGTCGACATCCGCAC-3') (SEQ ID NO:5).

RT-PCR Analysis for Transposase Gene Expression

RNA extracted from T0 transgenic rice calli was reverse transcribed with use of the SuperScript™ First Strand Synthesis System (Invitrogen). Primers specific to each of the two target sequences were used in subsequent PCR amplification: ER (5'-ACAGGGCCCTCATGG AGAGGAGCC-3') (SEQ ID NO:6) and CHC2 (5'-ATACAAGTCAACTGTTGCTTC-3') (SEQ ID NO:7) for Ac transposase.

Induction of KCEH Transposition and the Determination of Insertion Sites

For induction experiments, T1 rice seeds of each transformed line harboring a single copy of KCEH were incubated on callus induction medium (CIM) containing hygromycin for 4 weeks in order to yield enough calli for the induction experiments. 5 mM of SA was previously found to have the highest induction efficiency in transgenic rice containing a PR-1a-based transposon (Charng et al., The inducible transposon system for rice functional genomics. 2007, Bot Stud 48:1-11), so transposition was induced by incubating transgenic rice calli harboring the KCEH system on CIM containing 5 mM of SA. The empty donor sites of transposition were determined with the primers CAMBIA1 (5'-GTC-GACTTTCTAGAGGATCCG-3') (SEQ ID NO:8) and mKRT2R (5'-CAAGGAAACAGTCGACATCCGCGT-3') (SEQ ID NO:3).

The flanking sequences of the KCEH element in transgenic plants were amplified by TAIL-PCR with the following oligonucleotide primers: 3-1 (5'-GTGTGCTCCAGATTTATA TGG-3') (SEQ ID NO:9), 3-2 (5'-GATTTCGACTTTAAC-CCGACCGGA-3') (SEQ ID NO:10), and 3-3 (5'-CGTTTTCGTTA CCGGTATATCCCG-3') (SEQ ID NO:11) for the 3' end. The arbitrary degenerate (AD) primers and TAIL-PCR were as described previously (Sha et al., Generation and flanking sequence analysis of a rice T-DNA tagged population, 2004, Theor Appl Genet. 108: 306-314), with following modification: the primary TAIL-PCR contained approximately 150 ng of rice genomic DNA.

Induction of COYA Transposition

For experiments inducing COYA, the T1 rice seeds of each transformed line were incubated on callus induction medium containing hygromycin for 4 weeks to yield enough calli. $Hyg^R$ calli were incubated with 5 mM salicylic acid (SA) for 7 days, then transferred to callus induction medium without SA for 4-8 weeks before LUC or PCR analysis. To induce rice plants, transgenic rice at 3-leaf age were cultured in pods for a month, then flooded in 5 mM SA solution for 2 days/week until heading.

In Vivo and In Vitro Assays for Luciferase Gene Activity

In vitro activity of luciferase enzyme was determined by use of a Lumat LB 9501 luminometer (Berthold, Munchen, Germany). For in vivo assay, 0.15 mg/l of luciferin aqueous solution was applied to rice calli, which were then placed in a dark room, then analyzed by use of a luminometer with an intensified CCD camera (Hamamatsu, Japan) and a Nikon 35-mm lens connected to a computer. The plant material and luminescent images were taken separately, the luminescent images revealing calli with luciferase activity.

PCR Analysis of COYA Excision Events

Transposition of COYA from the COYA::LUC construct in transgenic plants was analyzed by PCR with oligonucleotide primers: primer 35S (5'-TCCTTCGCAAGACCCTTCCT-3') (SEQ ID NO:12); and primer LUC2 (5'-CGGGCGCAACT-GCAACTCC-3') (SEQ ID NO:13).

The flanking sequences of the T-DNA or COYA integration sites in transgenic plants were determined by use of arbitrary degenerate (AD) primers and TAIL-PCR as described previously (Sha et al., Generation and flanking sequence analysis of a rice T-DNA tagged population, 2004, Theor Appl Genet. 108: 306-314), with modification: the primary TAIL-PCR involved approximately 150 ng of rice genomic DNA. The flanking sequences were amplified with the following oligonucleotide primers: CA1 (5'-TAGGGTTTCGCTCATGT-GTT-3') (SEQ ID NO:14), CA2 (5'-GTGTTGAGCATATAA-GAAACCCT-3') (SEQ ID NO:15) and CA3 (5'-TTCGGCGTTAATTCAGTACA-3') (SEQ ID NO: 16) for T-DNA and 3-1 (5'-GTGTGCTCCAGATTTATATGG-3') (SEQ ID NO:9), 3-2 (5'-GATTTCGACTTTAACC CGAC-CGGA-3') (SEQ ID NO:10) and 3-3 (5'-CGTTTTCGTTAC-CGGTATATC CCG-3') (SEQ ID NO:11) for the 3' end.

Isolation of Genomic DNA and Southern Blot Analysis

Genomic DNA was isolated from transformed plants by use of a kit (Genemark, Tainan, Taiwan). In brief, fresh leaves (2 g) or callus tissue (0.1 g) was frozen in liquid nitrogen and ground with use of a mortar and pestle. Nuclei were isolated and lysed by protease treatment, and genomic DNA was precipitated with ethanol and dissolved in TE buffer (10 mM Tris-HCl, 1 mM EDTA; pH 8.0). About 10 μg of each DNA was digested with the appropriate restriction enzyme under the conditions specified by the suppliers and fractionated on 0.8% agarose gels (in 1×TAE) overnight at 1 V/cm. Southern blot analysis was performed as described.

Example 1

Construction of the Transposon-Mediated Marker-Off System

Figure 3:
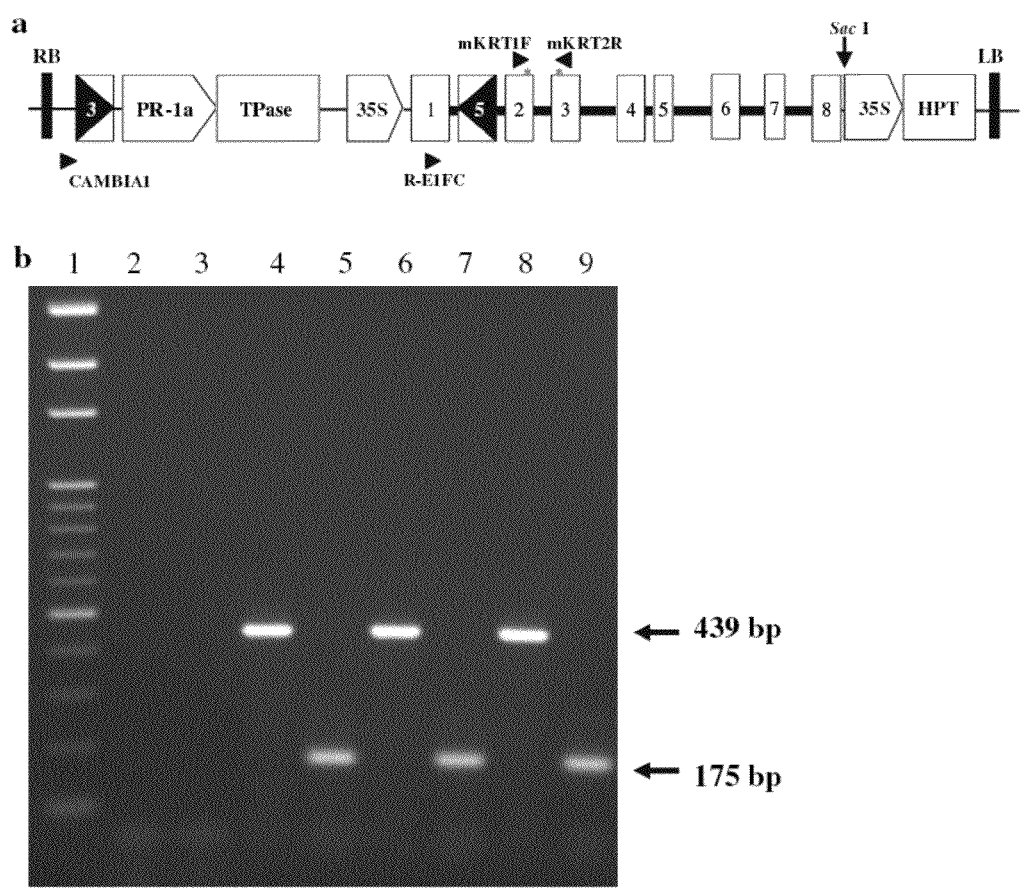
FIG. 3 shows (a) Schematic representation of the KCEH system and the location of primers (shown as solid triangles). LB, left border; RB, right border; 5' and 3', Ac left and right terminalinverted repeat; PR-1a, inducible promoter; TPase, transposase gene; 35S, cauliflower mosaic virus 35S RNA promoter; 1~8=epsps exon 1~-exon 8; bold lines, epsps introns; *mutation site. (b) Reverse transcriptase polymerase chain reaction (RT-PCR) analysis of modified (or endogenous) epsps expression in transgenic rice (lanes 4, 5, 8, 9) or wild type (lanes 2, 3, 6, 7) with primers R-E1FC and mKRT2R (lanes 2 and 4), mKRT1F and mKRT2R (lanes 3 and 5), R-E1FC and KRT2R (lanes 6 and 8), KRT1F and KRT2R (lanes 7 and 9). Lane 1:100-bp marker.

The construction of the inducible transposon system to truncate the marker gene was depicted in FIG. 3a. First, the 5' end of the Ac element was inserted in the first intron of the rice genomic epsps driven by the CaMV35S promoter, which had been modified to produce a glyphosate-tolerant form of the enzyme. To complete a new transposon, a PR-1a::TPase fusion was flanked by the 3' end of Ac. The new transposon, KCEH, contains a PR-1a::TPase fusion, a CaMV35S promoter, and the first exon of the modified epsps. The KCEH system (KCEH transposon plus the marker gene) was inserted into the binary vector pCAMBIA 1300, yielding the plasmid pKCEH, which was introduced into the *Agrobacterium tumefaciens* strain LBA4404 for plant transformation.

Expression of the Modified epsps in Transgenic Rice Plants

To determine the behavior of the modified epsps in rice, the KCEH construct was transformed into rice, with hygromycin used as the selection agent. A total of 21 single-copy transgenic lines were determined by PCR and DNA blot analysis (data not shown), and the total RNA of each line was extracted for RT-PCR. The modified epsps in the KCEH construct and endogenous rice epsps differ in 4 bp. To eliminate the possibility of amplifying the endogenous rice epsps, we designed two primers, mKRT1F and mKRT2R, which were specific to the modified sites of epsps. These two primers are mismatched at the two 3' terminal bases for endogenous epsps and have more power to identify transgenes. To ensure functional splicing of the first intron by PCR, the primers RE1FC and mKRT2R were designed from the first and third exons of the modified epsps. In normal splicing of the endogenous epsps, the predictive fragment is 439 bp (FIG. 3b). With mKRT1F and mKRT2R, only modified epsps could be amplified by PCR, and the predicted fragment 175 bp was amplified (FIG. 3b). The experiments were performed again but primers mKRT1F and mKRT2R were replaced with primers KRT1F and KRT2R, which are matched for endogenous epsps. With these two primers, the expected DNA fragments could be amplified in transgenic rice, as well as in wild type TNG67.

Efficient *Agrobacterium*-Mediated Transformation of Rice with Modified epsps

Figure 4:
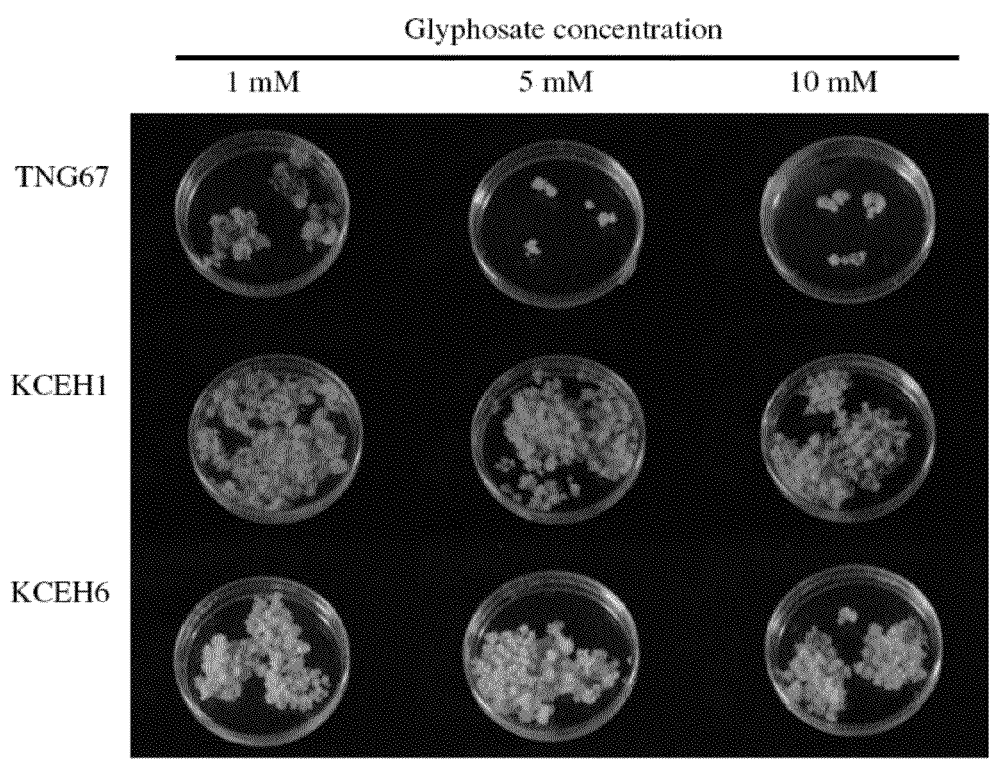
FIG. 4 shows determination of the glyphosate concentration of the modified epsps as a selective marker. Each line was cultured in callusinduced medium under different concentrations of glyphosate (1, 5, and 10 mM) for 5 weeks. KCEH-H1 and KCEH-H6 are independent transgenic lines with hygromycin used as the selection agent. TNG67, wild-type rice.

To determine whether the modified epsps can be used as a selectable marker in rice, the regenerated calli of transgenic lines containing a single copy of the modified epsps and the wild type were incubated with CIM containing glyphosate (1, 5, or 10 mM) for 4 weeks. FIG. 4 showed the tolerance of transgenic calli lines up to 10 mM of glyphosate, with the growth of wild-type calli extremely restricted on media containing 5 mM or 10 mM of glyphosate. Thus, 5 mM of glyphosate was used as the selection condition for rice transformation.

Figure 5:
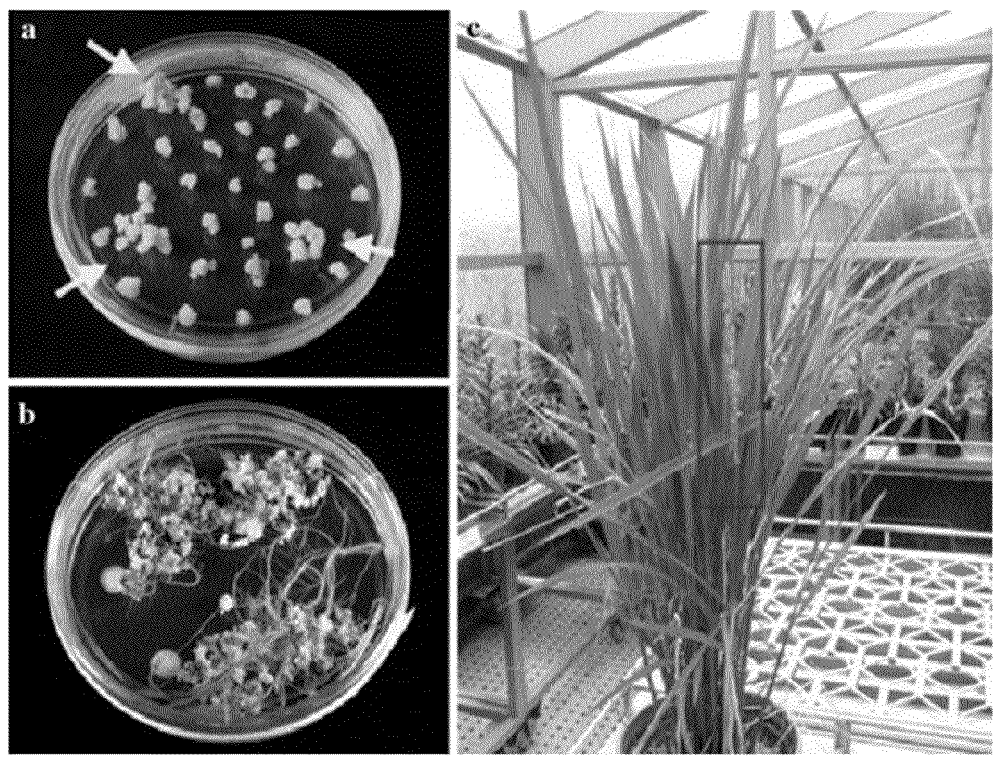
FIG. 5 shows different periods in the modified rice epsps transformation system. (a) Proliferation of calli in 5-mM of glyphosate growth medium over 5 weeks (arrows). (b) Differentiation of proliferating calli into shoots and roots in shooting medium over 5 weeks. (c) Transformants were transferred to soil for 2 months, grew well, and headed normally (box).
Figure 6:
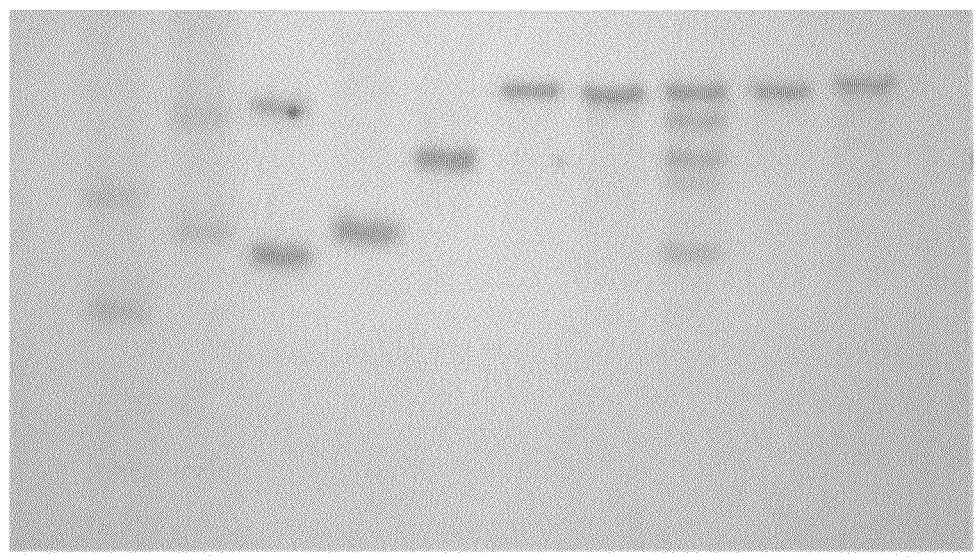
FIG. 6 shows analysis of T-DNA copies of transgenic rice selected by 5 mM of glyphosate. Instead of the use of modified epsps, hpt was used as a probe for DNA blot analysis because of the presence of endogenous epsps. W, wild type TNG67 rice; 1-20 represent the selected plants from T0 glyphosate-tolerant transformants. The single-copy T-DNA transgenic lines were re-numbered for subsequent analysis.
Figure 6:
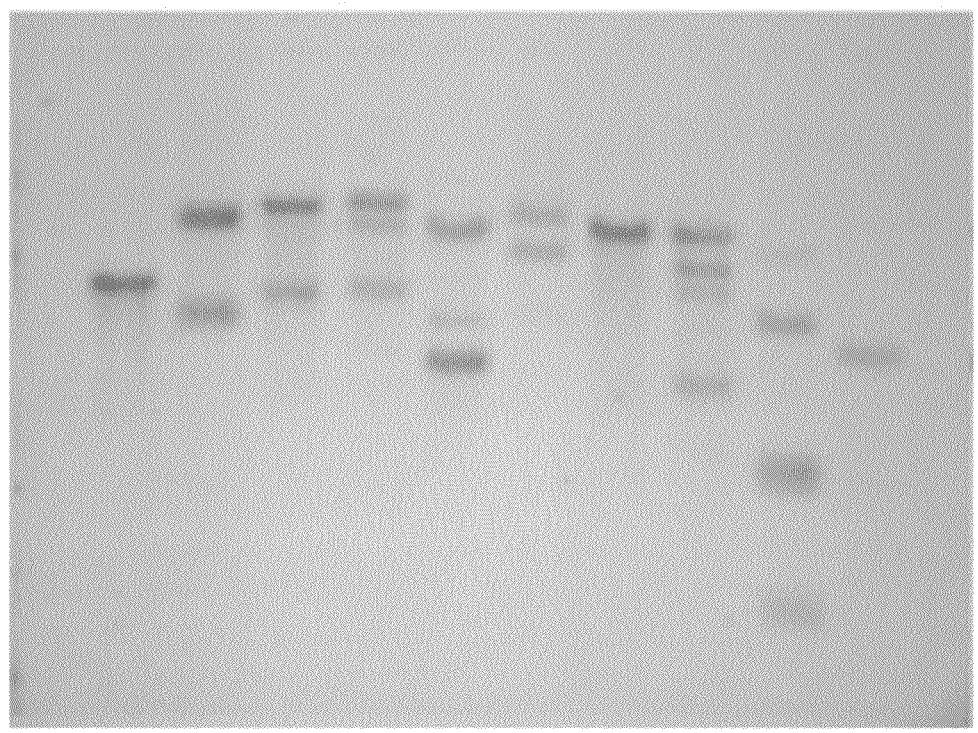

The pKCEH construct was introduced into the embryonic calli of rice, and transgenic plants were screened with use of 5 mM of glyphosate. The transgenic calli differed from non-transgenic calli by their proliferation potential under glyphosate treatment (FIG. 5*a*). The transgenic calli were transferred to differentiation medium to set shoots (FIG. 5*b*), then, the resulting plantlets were transferred to the soil and grown in the greenhouse to set seeds (FIG. 5*c*). We obtained 98 transgenic lines derived from 1,086 calli pools, for 9.02% transformation efficiency. To verify stable transformation, Sac I-digested genomic DNA from each independent transgenic line underwent Southern blot analysis. Since the modified epsps differs from the endogenous epsps by only 4 bp, we used the 1.1-kb fragment of the hpt gene as a probe. As an example, in FIG. 6, 9 of 20 transgenic lines contained only one T-DNA copy and the others more than two copies. From 98 transgenic lines, 43 single-copy independent transgenic rice lines were obtained, which indicates that the selection procedure is suitable for creating singlecopy lines. To determine the inheritance of the modified epsps and whether the transgenic rice plants were resistant to Roundup® (glyphosate applied in the field), mature rice seedlings from the T1 progeny were sprayed with 5,000 ppm Roundup®. We observed the expected 3:1 Mendelian ratio for the modified epsps among all single-copy T-DNA transgenic lines (data not shown; another progeny assay result is described below). Thus, the glyphosatetolerant phenotype was inherited as a single Mendelian locus in all of the plants tested. All of these results indicate that the modified epsps is suitable as a selectable marker in rice.

Figure 7:
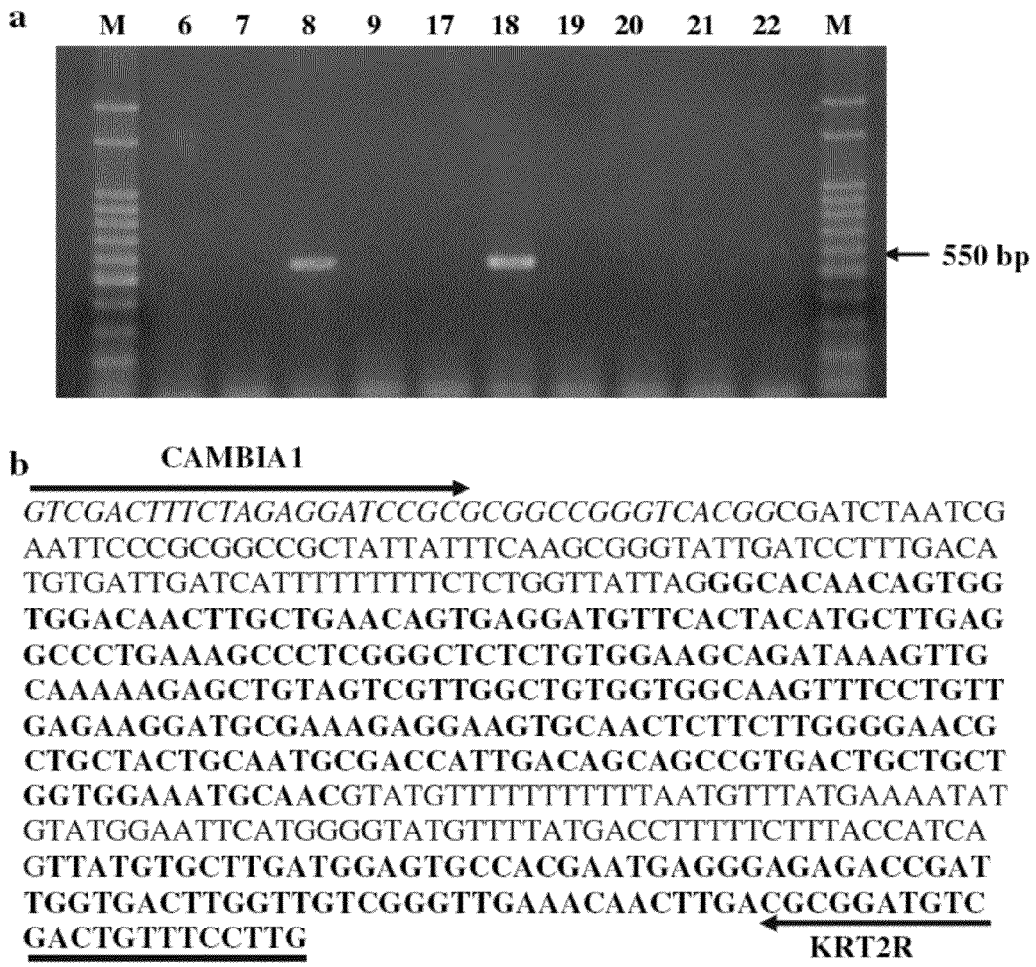
FIG. 7 shows analysis of transposition events of the SA-induced transgenic rice harboring KCEH system. (a) PCR analysis of KCEH transposition with the primers CAMBIA1 and mKRT2R and the expected fragments. (b) Sequence of the empty donor site of the transposition events, leaving the sequences from CAMBIA vector (italics) and the truncated epsps, in which the exons are shown in bold. The primers CAMBIA1 and mKRT2R are indicated as arrows. M=100-bp marker

Transposition of KCEH and Termination of the Glyphosate-Tolerant epsps in Transgenic Rice In Charng et al. The inducible transposon system for rice functional genomics. 2007, Bot Stud 48:1-11, an Ac-based inducible transposon, INAc, was introduced into rice and found that the highest transposition efficiency was induced with 5 mM of SA. Thus, to remove the functional glyphosate-tolerant epsps, 5 mM of SA was applied to transgenic rice calli to trigger the KCEH transposon. Calli regenerated from the T1 rice seeds of each transformed line harboring a single copy of KCEH were incubated on CIM containing 5 mM of SA to induce transposition. The excision events were determined by PCR with the primers mKRT2R and CAMBIA1. To determine the empty donor site, a 550-bp DNA fragment was expected (FIG. 7*a*). Of 43 single-copy lines, seven transgenic lines yielded the expected 550-bp DNA products, for 16% somatic transposition efficiency. Sequencing analysis confirmed the residual DNA after the excision of the transposon (FIG. 7*b*).

According to Charng et al. The inducible transposon system for rice functional genomics. 2007, Bot Stud 48:1-11, Ac-based inducible transposons were very active in induced rice calli, but, sometimes, only a portion of cells contain the empty donor site (partial transposition events; Charng et al., The inducible transposon system for rice functional genomics. 2007, Bot Stud 48:1-11). We determined whether the transposition events passed through the germ line and were inherited in the progeny (germinal transposition) or not (somatic transposition). The remaining calli of the transposed lines, as well as non-SA-treated calli (controls), were cultured to set shoots and then transplanted to soil for self-pollination. The seedlings of the progeny underwent PCR to determine the inheritance of the transposition events. Of seven lines showing transposition, only two showed the transposition events inherited in the progeny. The seedlings of the progeny were treated with Roundu® as described above. All 25 seedlings were glyphosate-sensitive, which indicates the loss of the glyphosate-tolerant function (FIG. 8 left).

Figure 8:
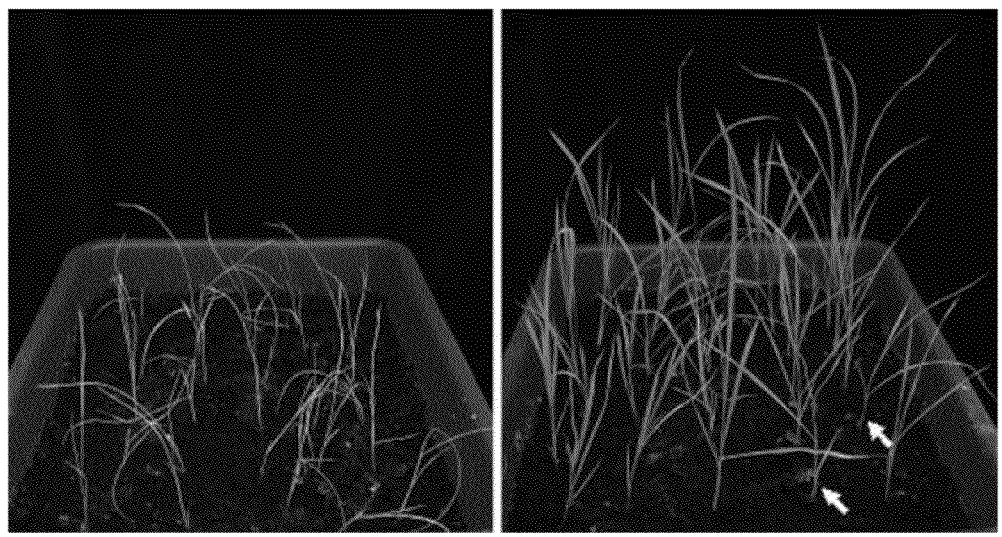
FIG. 8 shows glyphosate-tolerance analysis of the self-pollinated progeny of KCEH transposed (left) and untransposed line (right). The arrows indicate the null KCEH progeny, which are not resistant to glyphosate.

As a control, siblings of the same transgenic line which had not been induced with SA for transposition were cultured to harvest self-pollinated seeds for glyphosate-tolerant assay and showed glyphosate-tolerance as a single Mendelian locus pattern (FIG. 8 right).

Genomic DNA containing the independent transposed KCEH was collected to amplify the flanking sequences of the transposed KCEH elements. The flanking sequences were isolated by TAIL PCR. A summary of the significant homologies obtained after comparison of the flanking sequences from a public database is shown in Table 1. Of six independent transposition events, four showed linkages and one no linkage to the T-DNA locations. For one event, the flanking sequence was not obtained, possibly because of failure to amplify the PCR product or loss of the transposon after excision from its donor site. Taken together, the results indicate that the KCEH system offers a desirable selectable marker for rice transformation and the ability to remove the marker thereafter.

TABLE 1

Genomic sequences flanking KECH insertions in transgenic rice plants. The T-DNA integration site of each line is indicated after its designation

| Line | Chromosome | BACs/PACs | Insertion position (bp) | GenBank accession no. | Identities |
| --- | --- | --- | --- | --- | --- |
| K-08 (21) | (T-DNA) 10 | OSJNBb0060I05 | 56901 | AC092697 | 86/86 (100%) |
|  | (KCEH) 10 | OSJNBa0040D23 | 32948 | AC074196 | 102/102 (100%) |
| K-18 (12) | (T-DNA) 3 | OSJNBa0039F10 | 52992 | AC137931 | 127/128 (99%) |
|  | (KCEH) 3 | OSJNBa0045E22 | 156408 | AC137072 | 217/217 (100%) |
|  | (KCEH) 8 | OSJNBb0092C08 | 74311 | AP005391 | 251/251 (100%) |
| K-26 | (T-DNA) 4 | OSJNB0022F23 | 130273 | AL606447 | 227/227 (100%) |
|  | nd | nd | nd | nd | nd |
| K-34 | (T-DNA) 11 | OSJNBa007P22 | 82765 | AC109594 | 256/256 (100%) |
|  | (KCEH) 11 | OSJNBa0007P22 | 143401 | AC109594 | 198/198 (100%) |
| K-40 | (T-DNA) 5 | OJ1362_D02 | 120545 | AC105770 | 308/316 (97%) |
|  | (KCEH) 5 | OJ1281_H05 | 30721 | AC117265 | 290/290 (100%) | nd = no detectable product obtained after TAIL PCR amplification

Example 2

Construction of the One-Time Transposon System COYA

Figure 2:
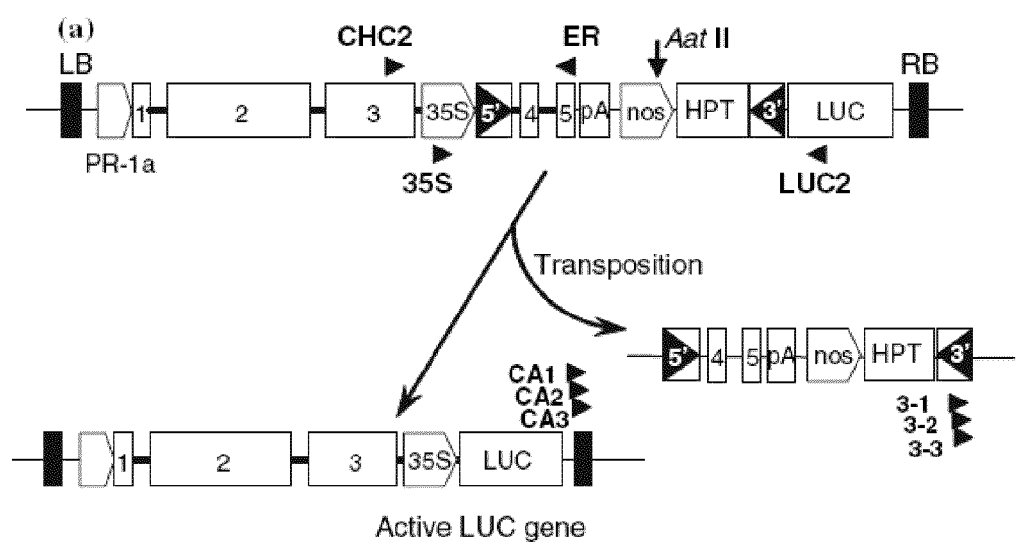
FIG. 2 shows schematic diagram of the one-time COYA transposon system and location of primers (shown as solid triangle). LB, Left border; RB, right border; 5' and 3', Ac left and right terminal-inverted repeat; PR-1a, PR-1a inducible promoter; HPT, hygromycin phosphotransferase gene; pA, poly(A) fragment; NOS, nopaline synthase promoter; LUC, luciferase gene; 1-5, transposase gene exon 1-exon 5.

The construction of the one-time transposon system COYA is described in FIG. 2. First, the 5' end of the Ac element, together with a 35S promoter, was inserted into the third intron of the transposase gene, driven by a PR-1a promoter from tobacco. Then, the 3' end of the Ac element flanking the hygromycin phosphotransferase (HPT) gene was constructed downstream of the transposase gene. Hence, the transposon contained the fourth and fifth exons of the transposase gene and HPT. Furthermore, the COYA element was constructed between the 35S promoter and the LUC gene. In principle, after transposition, LUC could be reactivated and the transposase gene would be truncated. The COYA system was inserted into the binary vector pCAMBIA 2200, yielding the plasmid pCOYA, which was then introduced into rice plants by use of transfection with *Agrobacterium tumefaciens* strain LBA4404. We used 21 single-copy T-DNA integration transgenic plants for the induction and detection of transposition events.

Normal Expression of Transposase Gene with COYA

Figure 9:
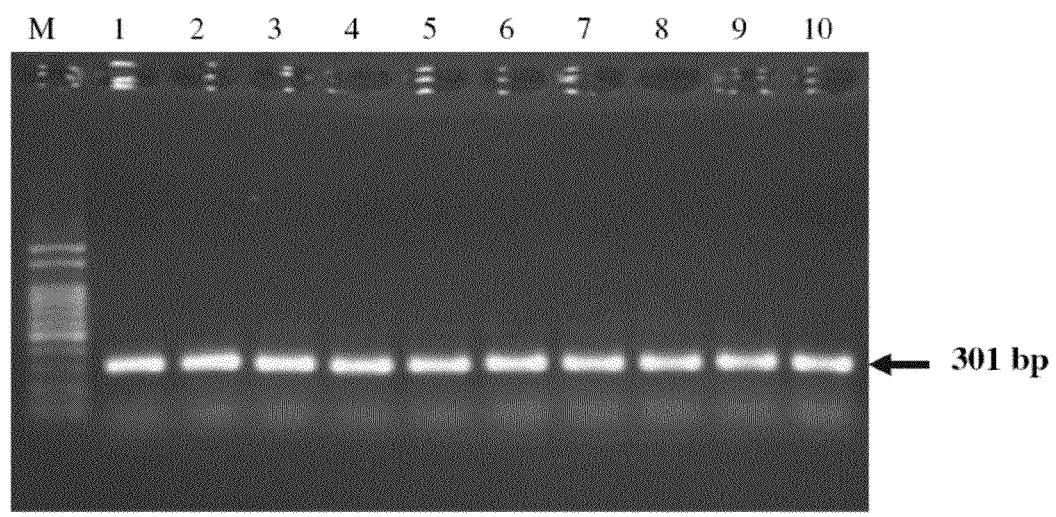
FIG. 9 shows RT-PCR analysis of induced transposase gene expression in transgenic rice lines (1-10) with the primers CHC2 and ER. M=100 bp marker.

To determine whether the Ac transposase gene COYA was expressed successfully in transgenic rice, singlecopy transgenic rice calli generated from T1 seeds were incubated with callus induction medium containing 5 mM SA for 7 days, then the total RNA of each transgenic rice line was extracted for RT-PCR. Two specific primers, CHC2 and ER (FIG. 2), were used to determine functional splicing. As predicted, a 301-bp DNA fragment was obtained (FIG. 9). Sequencing analysis suggested a normal expression of transposase gene with COYA (data not shown).

Transposition Events of COYA in Transgenic Rice

Figure 10:
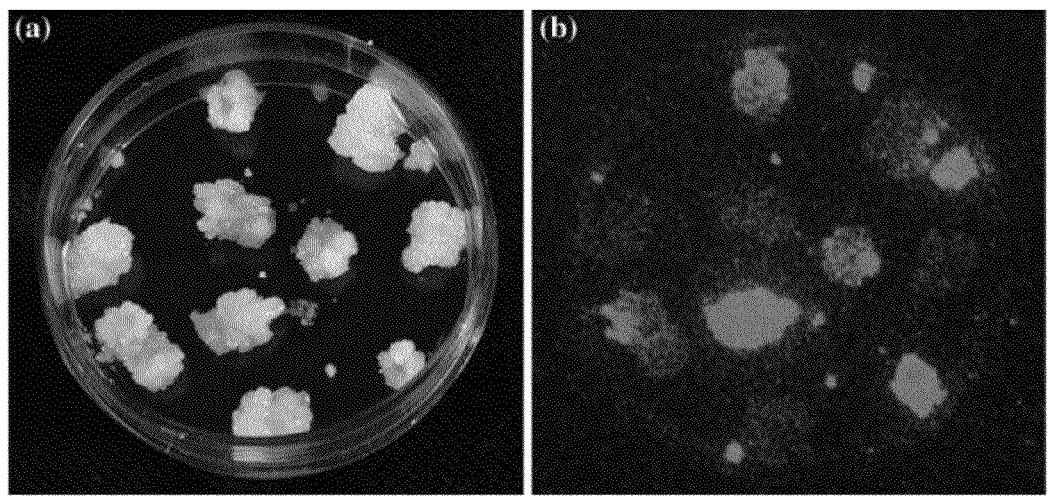
FIG. 10 shows analysis of transposition events of SA-induced transgenic rice harboring COYA system. (a) Reflected-light image of induced transgenic rice calli harboring COYA system and (b) its luminescence image.
Figure 11:
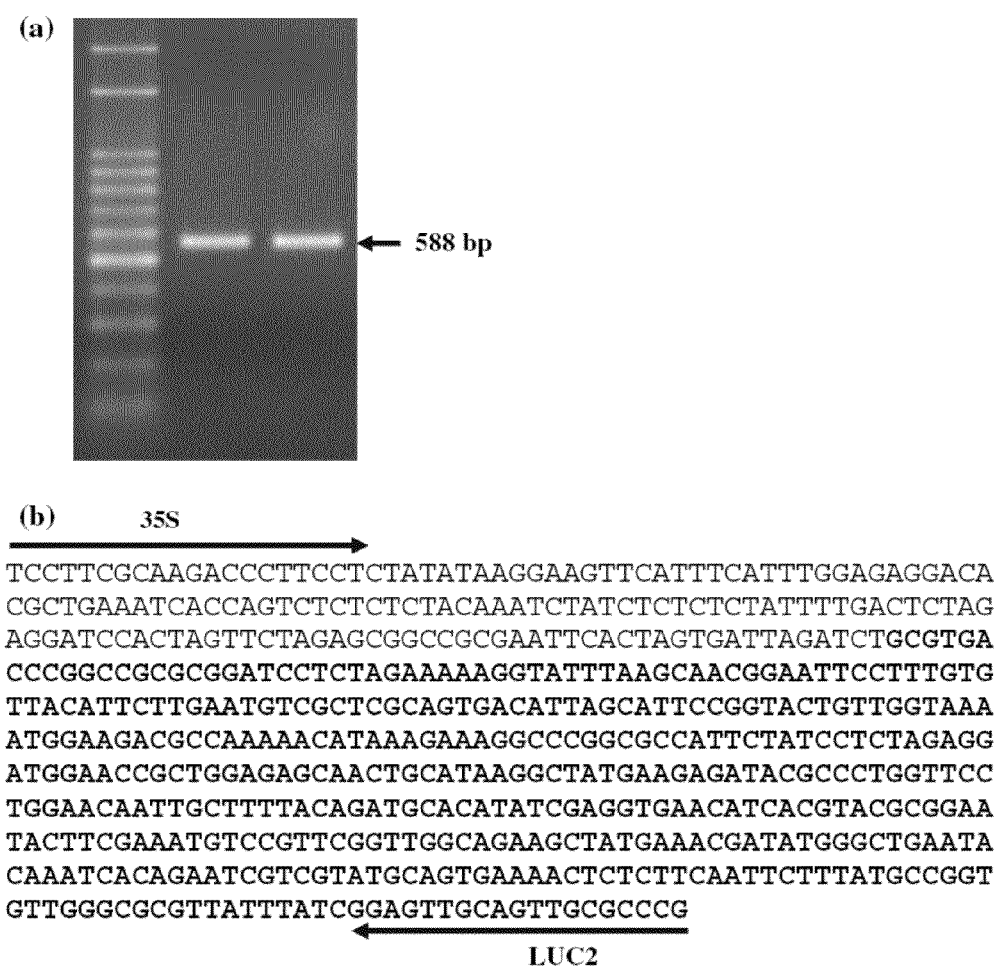
FIG. 11 shows analysis of spontaneous transposition events of transgenic rice harboring COYA system. (a) PCR analysis of COYA transposition using primers 35S and LUC2 and the expected fragments. (b) Sequence of the empty donor site of the transposition events. The sequences flanking the COYA 5' end are shown in bold.

Since the transposase gene could be expressed normally after 7 days' induction, SA-induced calli were then cultured on normal medium for further regeneration to determine whether the COYA transposition events could also be induced in rice calli. Transposition events were detected by in vivo LUC assay and PCR, then sequencing analysis. First, induced calli incubated with luciferin underwent direct LUC image capture (FIGS. 10a and b). Then, two primers for PCR reaction were designed to confirm the excision of COYA. To determine the empty donor sites after excision, the primers 35S and LUC2, which are specific to DNA sequences flanking each end of COYA were used. After PCR amplification, a 588-bp DNA fragment was obtained (FIG. 11a) and sequenced to confirm the empty donor site (FIG. 11b).

Next, we tested the transposition efficiency of COYA. Transposition events were determined by in vitro LUC assay and PCR analysis described above. In $Hyg^R$ rice calli regenerated from T1 seeds of each transgenic line, treatment with SA induced transposition of COYA, as analysed by in vitro LUC assay and PCR, and the transposition efficiency was dose dependent (Table 2). Approximately 9% of COYA transposition events were spontaneous. Treatment with SA resulted in a high level of transposition efficiency; 52% for 5 mM SA and 76% for 10 mM SA (Table 2). Thus, with insertion of the third intron of the transposase gene by a DNA fragment containing a 35S promoter and the 3' end of Ac, the transposase gene could express and target normally both ends of Ac with high efficiency.

Germinal Transposition of COYA in Transgenic Rice

An important feature of an inducible transposable element is its ability to induce transposition in germinal tissue or in somatic tissues, which allowed the transposition event to pass through the germ line and be inherited in the progeny. Such ability markedly increases the success of transposon tagging in isolating important plant genes. To determine the effectiveness of COYA for gene tagging in rice, transposition was induced in adult rice plants of eight transformed lines, which revealed no spontaneous transposition but, rather, SA-induced transposition (Table 2). Since rice floral tissues embed in the flag leaves when (or before) meiosis occurs, transgenic rice with 5 mM SA solution 2 days/week was flooded until seed set. The germinal transposition events/efficiencies were determined by the following steps: (1) LUC assay (in vitro) and PCR analysis to determine the presence of empty donor sites in progeny, which reveals the germinal transposition efficiency; (2) DNA blot analysis to identify each independent transposition events and thus determine the germinal transposition efficiency; and (3) flanking sequence analysis of each re-integrated COYA to reveal the transposition pattern of this one-time inducible transposon.

Of 1,065 seedlings, 273 (25.6%) exhibited luciferase activity and yielded PCR-specific products (Table 3). Among transformed plants without SA treatment, 376 seedlings yielded neither luciferase activity nor PCR-specific products for the empty donor site.

Figure 12:
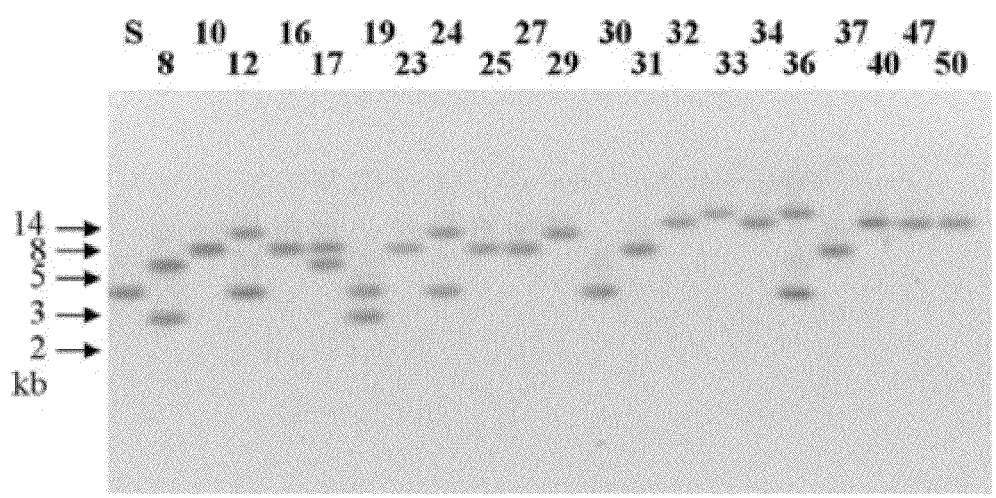
FIG. 12 shows Southern blot analysis of hygromycin-resistant COYA plants from a single starter line (Y-20) using the HPT gene as a probe. S, starter line; numbers represent selected plants from 21 independent Y-20 families after primary Southern blot analysis. Size markers after ethidium bromide staining are indicated on the left.

LUC assay revealed the efficiency of COYA excision events that transmitted to progeny. Still, a single transposition event could happen early during rice growth and be inherited in many progeny, with siblings consequently containing the same COYA integration sites. This feature would lead to overestimation of the transposition efficiency. To rule out this possibility, independent events were identified. Since the results shown in Table 3 indicated that lines Y-12 and Y-52 yielded relatively low transposition frequencies, the six other lines were used. First, COYA (transposed or untransposed) in progeny determined by hygromycin resistance assay (data not shown) revealed out of 859 transgenic rice plants, 635 $Hyg^R$, which were selected for further analysis. The frequency and pattern of COYA transposition in transgenic rice were detected by Southern blot analysis, with the HPT gene used as a probe. Aat II digestion of the genomic DNA resulted in a unique hybridizing band, depending on the line (e.g., 4.2 kb for line Y-20 Starter line), which corresponded to the presence of an un-transposed COYA element (FIG. 12). A novel band of distinct size in progeny plants was considered an independent transposed COYA element. As an example, shown in FIG. 12, 21 progeny yielded 27 hybridizing signals composed of seven independent transposition events. Of 859 progeny assayed, 80 yielded COYA-reintegrated bands, with 27 independent integration signals (Table 3). Southern blot analysis revealed that all transformed lines used for germinal transposition experiments were heterozygous for the COYA T-DNA insertion site (FIG. 12; and data not shown). Since COYA was constructed for one-time transposition, the stability of the transposed COYA was determined with progeny of plants harboring single transposed COYA (e.g., lines 29 and 31; FIG. 12). Again, Southern blot analysis to detect the unique hybridizing band of COYA revealed all assayed progeny with the same hybridization patterns as their control samples (data not shown). Therefore, it proved that the COYA element is self-stabilizing after transposition. The experiments were expanded to amplify the flanking sequences of the transposed COYA elements. Genomic DNAs containing the independent transposed COYA were collected as revealed by Southern blot patterns. The flanking sequences were isolated by TAIL PCR. A summary of the significant homologies obtained after comparison of the flanking sequences in a public database is shown in Table 4. For 27 independent transpositions, 16 were linked to the T-DNA locations, and 8 were un-linked. For three transposition events, the insertion locations were unclear, since the flanking sequences were matched to the repeat sequences in the database. Taken together, these results indicate that the transposase gene could be expressed functionally, then could cis-activate the COYA transposon for one time.

TABLE 2

Transposition efficiencies of calli derived from progeny of 21 single-copy transgenic lines harboring the COYA transposon

| Plant | None | Treatment 5 mM SA (5 days) | 10 mM SA (3 days) |
|---|---|---|---|
| Y-2 | 3/30 | 21/30 | 28/30 |
| Y-3 | 1/30 | 3/30 | 5/30 |
| Y-7 | 4/30 | 9/30 | 22/30 |
| Y-10 | 2/30 | 10/30 | 16/30 |
| Y-11[a] | 1/30 | 19/30 | 28/30 |
| Y-12[a] | 0/30 | 10/30 | 29/30 |
| Y-15 | 6/30 | 8/30 | 27/30 |
| Y-20[a] | 1/30 | 17/30 | 25/30 |
| Y-23[a] | 0/30 | 16/30 | 30/30 |
| Y-26[a] | 0/30 | 26/30 | 29/30 |
| Y-27 | 8/30 | 20/30 | 18/30 |
| Y-32[a] | 0/30 | 13/30 | 25/30 |
| Y-38 | 9/30 | 28/30 | 30/30 |
| Y-40[a] | 0/30 | 16/30 | 24/30 |
| Y-43 | 2/30 | 12/30 | 13/30 |
| Y-46 | 0/30 | 2/30 | 14/30 |
| Y-47 | 8/30 | 20/30 | 22/30 |
| Y-48 | 5/30 | 25/30 | 26/30 |
| Y-52[a] | 0/30 | 16/30 | 26/30 |
| Y-62 | 4/30 | 17/30 | 21/30 |

TABLE 2-continued

Transposition efficiencies of calli derived from progeny of 21 single-copy transgenic lines harboring the COYA transposon

| Plant | None | Treatment 5 mM SA (5 days) | 10 mM SA (3 days) |
|---|---|---|---|
| Y-65 | 3/30 | 15/30 | 19/30 |
| Mean (%) | 9 | 52 | 76 |

The regeneration calli derived from seeds of each line were divided into three portions for each treatment then incubated for 4 weeks before determination
All treatments were tested with a randomized collection of 30 samples for LUC and PCR analysis
Transportation events were recorded by the existence of LUC activites and PCR products described in "EXAMPLE 1"
[a]These lines were selected for induction of germinal transportation experiments

TABLE 3

Number of plants with COYA excision, transposition in the progeny of transgenic lines treated with SA

| Plant | Non-SA (control)[a] | SA-induced Tested | Excision[b] | Transposition | Independent transposition |
|---|---|---|---|---|---|
| Y-11 | 0/48 | 127 | 34 | 18 | 5 |
| Y-12 | 0/50 | 110 | 9 | nd | nd |
| Y-20 | 0/50 | 160 | 56 | 21 | 7 |
| Y-23 | 0/50 | 232 | 38 | 15 | 5 |
| Y-26 | 0/50 | 212 | 42 | 13 | 6 |
| Y-32 | 0/46 | 138 | 68 | 10 | 3 |
| Y-40 | 0/50 | 140 | 22 | 2 | 1 |
| Y-52 | 0/32 | 96 | 4 | nd | nd |
| Total | (0%) | 1,065 | 273 (25.6%) | 80 (7.5%) | 27 (2.5%) |

[a]Number of LUC+ progeny of transgenic rice without SA treatment as control (number of LUC+/number tested)
[b]LUC assay was preliminary performed to reveal the excision efficiency. The results were used to exclude line Y-12 and 52 for Southern blot analysis
nd Southern analysis was not carried out

TABLE 4

Genomic sequences flanking COYA insertions in transgenic rice plants

| Line | Chromosome | BACs/PACs | Insertion position (bp) | GenBank accession no. | Identities |
|---|---|---|---|---|---|
| Y-11 | (T-DNA) 2 | OJ1191_G08 | 5415 | AP004047 | 68/68 (100%) |
| 11-11 | 1[a] | P0443D08 | 20572 | AP003250 | 280/280 (100%) |
| 11-12 | 2 | OJ1479_B12 | 82024 | AP004165 | 183/183 (100%) |
| 11-19 | 10 | OSJNBa0065C1 | 85441 | AC074354 | 333/333 (100%) |
| 11-22 | 2 | P0663F07 | 151215 | AP005823 | 48/48 (100%) |
| 11-29 | 2[a] | P0487D09 | 153603 | AP004880 | 56/56 (100%) |
| Y-20 | (T-DNA) 12 | OSJNBa0005P03 | 110785 | AL935066 | 34/34 (100%) |
| 20-8 | 6 | P0417E03 | 48819 | AP006054 | 198/198 (100%) |
| 20-8 | 12 | OSJNBa0073H17 | 28133 | AL713909 | 127/127 (100%) |
| 20-10 | 10 | OSJNBa0096E22 | 38484 | AC099400 | 138/138 (100%) |
| 20-12 | 12 | OSJNBa0090O14 | 7648 | AL731763 | 280/280 (100%) |
| 20-17 | 12 | OSJNBb0085B24 | 40635 | AL954871 | 83/83 (100%) |
| 20-32 | 12 | OSJNBa0011B18 | 104124 | AL713908 | 400/400 (100%) |
| 20-33 | 4 | OSIGBa0125J07 | 59068 | CR855046 | 75/75 (100%) |
| Y-23 | (T-DNA) 3 | OSJNBa0093I13 | 119497 | AC097279 | 184/184 (100%) |
| 23-2 | 3 | OSJNBb0081I10 | 52069 | AC134240 | 147/147 (100%) |
| 23-18 | 5 | OSJNBb0088P07 | 47841 | AC119292 | 124/124 (100%) |
| 23-22 | 3 | OSJNBa0076E06 | 17317 | AC132215 | 66/66 (100%) |
| 23-29 | 3 | OJ1125B03 | 98463 | AC134885 | 108/108 (100%) |
| 23-36 | 3 | OJ1125B03 | 93833 | AC134885 | 87/87 (100%) |
| Y-26 | (T-DNA) 9 | P0635G10 | 42087 | AP005396 | 334/334 (100%) |
| 26-5 | 8 | OJ1113_A10 | 78270 | AP004643 | 94/94 (100%) |
| 26-7 | 9[a] | OSJNBa0035B22 | 108545 | AC137592 | 89/89 (100%) |

TABLE 4-continued

Genomic sequences flanking COYA insertions in transgenic rice plants

| Line | Chromosome | BACs/PACs | Insertion position (bp) | GenBank accession no. | Identities |
| --- | --- | --- | --- | --- | --- |
| 26-18 | 9 | OSJNBa0035B22 | 101135 | AC137592 | 47/47 (100%) |
| 26-21 | 9 | OSJNBa0042B15 | 47964 | AP006170 | 50/50 (100%) |
| 26-22 | 12 | OJ1005_B07 | 34060 | AL713946 | 127/127 (100%) |
| 26-38 | 9 | P0489D11 | 7621 | AP005742 | 240/240 (100%) |
| Y-32 | (T-DNA) 10 | OSJNBa0040D23 | 133921 | AC074196 | 82/84 (98%) |
| 32-2 | 10 | OSJNBa0025B05 | 9103 | AC096782 | 124/124 (100%) |
| 32-8 | 5[a] | OSJNBa0032D15 | 45261 | AC120989 | 155/155 (100%) |
| 32-19 | 10 | OSJNBa0031A07 | 38533 | AC084884 | 200/200 (100%) |
| Y-40 | (T-DNA) 7 | OJ1119_B04 | 4292 | AP003943 | 186/186 (100%) |
| 40-11 | 7 | OJ1119_B04 | 87349 | AP003943 | 40/40 (100%) |

The T-DNA integration site of each line is indicated after its designation
[a]Indicates the flanking sequences matched to the repeat sequences in the database, and one record was singled out to present in this table While the invention has been described and exemplified in sufficient detail for those skilled in this art to make and use it, various alternatives, modifications, and improvements should be apparent without departing from the spirit and scope of the invention.

---

What is claimed is:

1. A genetic construct comprising:

a DNA cut-and-paste transposon genetic unit which comprises a first promoter which is inducible in plants, a transposase gene, a 5' inverted repeat sequence, which is located in an intron of the transposase gene, a poly(A) fragment, a transgene unit, and a 3' inverted repeat sequence which are operably linked in the 5' to 3' direction, wherein the transposase gene is operably under the control of the first promoter; and wherein the transgene unit comprises a second promoter and an expressable transgene which are operably linked in the 5' to 3' direction, wherein the transgene is operably under the control of the second promoter.

2. The genetic construct of claim 1, wherein the transposon is a maize Ac transposon, En/Spm transposon, Mutator (Mu) transposon, *Drosophila* P element, piggyBac transposon, or mice Sleeping Beauty (SB) transposon.

3. The genetic construct of claim 2, wherein the transposon is the maize Ac transposon.

4. The genetic construct of claim 3, wherein the transposase gene is an Ac transposase gene.

5. The genetic construct of claim 4, wherein the 5' and 3' inverted repeat sequences are Ac left and right terminal-inverted repeats.

6. The genetic construct of claim 1, wherein the first promoter is a PR-1a inducible promoter.

7. The genetic construct of claim 1, wherein the second promoter is a nopaline synthase promoter.

8. The genetic construct of claim 1, wherein the transgene is a selectable marker.

9. A method of transiently expressing a transgene in a stably transformed plant, comprising the following steps:

(a) stably transforming the plant with a genetic construct, comprising a DNA cut-and-paste transposon genetic unit which comprises a first inducible promoter, a transposase gene, an 5' inverted repeat sequence, which is located in an intron of the transposase gene, a poly(A) fragement, a transgene unit, and a 3' inverted repeat sequence which are operably linked in the 5' to 3' direction, wherein the transposase gene is operably under the control of the first promoter; and wherein the transgene unit comprises a second promoter and an expressable transgene which are operably linked in the 5' to 3' direction, wherein the transgene is operably under the control of the second promoter;

(b) expressing the transgene of the genetic construct in the plant; and (c) expressing the transposase gene of the genetic construct in the plant.

10. The method of claim 9, wherein the step (c) is inducible when the first promoter of the genetic construct is an inducible promoter, and a corresponding inducing agent of the inducible promoter is applied to the plant at the step (c).

11. The method of claim 9, wherein the plant is maize, rice, a fruit-bearing plant or a flowering plant.

12. The method of claim 9, wherein the transposase gene is able to be inducibly expressed only one-time.

13. The method of claim 9, wherein the first promoter is a PR-1a inducible promoter.

14. The method of claim 9, wherein the second promoter is a nopaline synthase promoter.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 1
atcgtgctcc agcccatcag        20

<210> SEQ ID NO 2
<211> LENGTH: 24
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(24)

<400> SEQUENCE: 2
caactcttct tggggaacgc tgct        24

<210> SEQ ID NO 3
<211> LENGTH: 24
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(24)

<400> SEQUENCE: 3
caaggaaaca gtcgacatcc gcgt        24

<210> SEQ ID NO 4
<211> LENGTH: 24
<212> TYPE: DNA
<213> ORGANISM: Artificial

```
<220> FEATURE:
<223> OTHER INFORMATION: primer synthesis
<220> FEATURE:
<221> NAME/KEY: misc_binding
<222> LOCATION: (1)..(24)

<400> SEQUENCE: 4
caactcttct tggggaacgc tgga                                              24

<210> SEQ ID NO 5
<211> LENGTH: 24
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(24)

<400> SEQUENCE: 5
caaggaaaca gtcgacatcc gcac                                              24

<210> SEQ ID NO 6
<211> LENGTH: 24
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(24)

<400> SEQUENCE: 6
acagggccct catggagagg agcc                                              24

<210> SEQ ID NO 7
<211> LENGTH: 21
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(21)

<400> SEQUENCE: 7
atacaagtca actgttgctt c                                                 21

<210> SEQ ID NO 8
<211> LENGTH: 21
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(21)

<400> SEQUENCE: 8
gtcgactttc tagaggatcc g                                                 21

<210> SEQ ID NO 9
<211> LENGTH: 21
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(21)
```

```
<400> SEQUENCE: 9
gtgtgctcca gatttatatg g                                         21

<210> SEQ ID NO 10
<211> LENGTH: 24
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(24)

<400> SEQUENCE: 10
gatttcgact ttaacccgac cgga                                      24

<210> SEQ ID NO 11
<211> LENGTH: 24
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(24)

<400> SEQUENCE: 11
cgttttcgtt accggtatat cccg                                      24

<210> SEQ ID NO 12
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 12
tccttcgcaa gacccttcct                                           20

<210> SEQ ID NO 13
<211> LENGTH: 19
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(19)

<400> SEQUENCE: 13
cgggcgcaac tgcaactcc                                            19

<210> SEQ ID NO 14
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 14
tagggtttcg ctcatgtgtt                                           20
```

```
<210> SEQ ID NO 15
<211> LENGTH: 23
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(23)

<400> SEQUENCE: 15
gtgttgagca tataagaaac cct                                        23

<210> SEQ ID NO 16
<211> LENGTH: 20
<212> TYPE: DNA
<213> ORGANISM: Artificial
<220> FEATURE:
<223> OTHER INFORMATION: primer synthesis
<220> FEATURE:
<221> NAME/KEY: misc_binding
<222> LOCATION: (1)..(20)

<400> SEQUENCE: 16
ttcggcgtta attcagtaca                                            20
```